United States Patent [19]
Plummer et al.

[11] Patent Number: 5,838,009
[45] Date of Patent: Nov. 17, 1998

[54] VARIABLE ANGLE MULTIPLE DETECTOR NUCLEAR MEDICINE GANTRY

[75] Inventors: Steven J. Plummer, Hudson; Jacin C. Barnes, Willowick, both of Ohio

[73] Assignee: Picker International, Inc., Highland Heights, Ohio

[21] Appl. No.: 757,874

[22] Filed: Nov. 27, 1996

[51] Int. Cl.⁶ .................................................. G01T 1/166
[52] U.S. Cl. ................................ 250/363.05; 250/363.04
[58] Field of Search ...................... 250/363.04, 363.02, 250/363.05, 363.08, 369

[56] References Cited

U.S. PATENT DOCUMENTS

| | | | |
|---|---|---|---|
| 4,213,054 | 7/1980 | Doherty, III | 250/363.04 |
| 4,409,484 | 10/1983 | Pinkstaff | 250/363 |
| 4,649,277 | 3/1987 | Terra et al. | 250/363.5 |
| 5,097,132 | 3/1992 | Plummer | 250/363.08 |
| 5,206,512 | 4/1993 | Iwao | 250/363.05 |
| 5,278,416 | 1/1994 | Pierfitte | 250/363.05 |
| 5,349,190 | 9/1994 | Hines et al. | 250/363.05 |
| 5,365,069 | 11/1994 | Eisen et al. | 250/370.09 |
| 5,444,252 | 8/1995 | Hug et al. | 250/363.08 |
| 5,523,571 | 6/1996 | Velazquez et al. | 250/363.05 |
| 5,569,924 | 10/1996 | Plummer | 250/363.05 |
| 5,717,212 | 2/1998 | Fulton et al. | 250/363.05 |

FOREIGN PATENT DOCUMENTS

2 697 918  5/1994  France .

*Primary Examiner*—Don Wong
*Attorney, Agent, or Firm*—T. B. Gurin; J. J. Fry

[57] ABSTRACT

A transformable gamma camera includes detectors mounted for circumferential movement with respect to a rotating gantry. The rotating gantry includes radial bores at desired angular positions about the rotating gantry. The stationary gantry includes a docking station such as a bore. A coupling mechanism allows the detectors to be coupled to the bores in the rotating gantry or to the docking station. Each of the detectors is movable radially with respect to the rotating gantry's axis of rotation and tangentially to the imaging region. The gamma camera is readily transformable between 120 degree, orthogonal, and opposed detector configurations; a plurality of aperture sizes can also be defined.

36 Claims, 9 Drawing Sheets

VARIABLE ANGLE MULTIPLE DETECTOR NUCLEAR MEDICINE GANTRY

BACKGROUND OF THE INVENTION

The present invention relates to the nuclear medicine art. It finds particular application in conjunction with multiple detector single photon emission computed tomography (SPECT) camera systems and will be described with particular reference thereto.

Early nuclear or Anger cameras had a single radiation detector head which was positioned stationarily over a region of interest of the subject The subject was injected with a radioactive dye which circulated through the patient's circulatory system. Some of the radiation given off by the dye was received by the gamma camera detector head which converted the radiation event into light.

More specifically, the detector head included a scintillation plate which converted each received radiation event into a scintillation or flash of light. An array of photomultiplier tubes positioned in the back of the scintillator plate and associated circuitry determined an (x,y) coordinate location and an energy of (z) value for each scintillation event A collimator including a grid-like array of lead vanes limited the path or trajectory of radiation events which could strike the scintillation plate. Typically, the collimator constrained each incremental element of the scintillator plate to be receptive only to radiation directly in front of it, i.e., radiation along paths substantially perpendicular to the scintillator plate. The collimator must be positioned as close to the patient as possible to acquire image data required to generate high resolution images. In this manner, a shadowgraphic image of the frequency of radiation events in the examined region of the subject was developed.

In SPECT imaging, the detector is rotated around the subject or indexed to a multiplicity of angularly offset positions around the subject to collect a data which is the mathematical equivalent of a CT scanner data set. More accurately, because the nuclear camera head is two-dimensional, a series of data sets are collected, each corresponding to one slice of an imaged volume.

Instead of a single detector head, other gamma cameras have two detector heads positioned on opposite sides of the subject. Placing two detector heads in this manner improves the resolution and data collection efficiency, particularly for whole body imaging. For other studies, particularly cardiac studies, it is advantageous to position the detector heads orthogonally to each other. This enables a complete 180 degree data set to be collected by rotating the pair of detector heads only 90 degrees relative to the subject. Still other gamma cameras have three heads placed at 120 degree intervals around the subject. Typically, the heads are movable radially toward and away from the patient and the three heads are rotatable, as a unit, around the patient. In each case, the detector face is placed as close as possible to the patient during.

Each of the foregoing systems has various advantages and disadvantages. The cost of a gamma camera system increases as additional detector heads are added. Systems having two opposed detector heads are particularly useful for whole-body imaging. Wide field of view detectors, which permit scanning of the entire width of the body, are preferably used in this application. Systems having two orthogonal detectors are commonly used for cardiac imaging. Because a wide field of view is not required in cardiac applications, smaller detectors are preferably used to allow the detectors to be placed as close as possible to the patient.

Three detector head systems are often used in connection with high resolution brain and cardiac imaging. Although wide field of view detectors are desirable for body imaging, their physical size again limits performance in head imaging. The placement of the three detector heads also limits the utility of three detector systems in whole body and brain applications.

These tradeoffs limit the versatility of traditional gamma camera systems. As a result, various attempts have been made to address them.

U.S. Pat. No. 5,444,252 to Hug, et al., issued Aug. 22, 1995 discloses a two detector system whereby the detectors are transformable between opposed and orthogonal positions. A separate driven mechanism and ring gear for each of the detectors increases the cost and physical complexity of the system. The minimum distance between the detectors and the patient in the orthogonal configuration, and hence system performance, is also limited by the physical size of the detector heads.

Co-pending U.S. application Ser. No. 08/292,785 discloses a system having two detectors which can be transformed between opposed and orthogonal configurations. Although the physical size of the detectors continues to limit the minimum distance between the patient and the detectors in the orthogonal configuration, this effect is reduced by offsetting the detector field of view from the center of rotation. This system is not readily adapted to a three detector configuration, however.

Co-pending U.S. application Ser. No. 08/635,390 discloses a three detector system where two of the three heads can be independently positioned about the gantry so that 120 degree three head, 180 degree opposed, and 90 degree orthogonal configurations can all be achieved. Although the physical size of the detector again limits the minimum distance between the detectors and the patient, the distance is reduced in the 90 degree orthogonal position by varying the angle from 90 degrees. The physical size of the detectors again limits the minimum distance between the detector faces and the patient in the 120 degree configuration.

The present invention provides a gamma camera which addresses the above-referenced shortcomings, and others.

SUMMARY

According to a first aspect of the present invention, a gamma camera includes a first member, a rotating gantry, two or more detectors, means for rotating the rotating gantry with respect to the first member, and means for selectively coupling at least one of the detectors to the first member and the rotating gantry.

According to more limited aspects of the invention, the means for selectively coupling includes a locking pin and the rotating gantry includes one or more bores which receive the locking pin.

According to another limited aspect of the invention, the gamma camera includes three detectors. The first detector is mounted in a fixed angular position with respect to the rotating gantry. The gamma camera also includes means for coupling the second and third detectors to the first member and to the rotating gantry.

According to yet other limited aspects of the invention, the detectors are movable in directions parallel and perpendicular to their faces. The gamma camera may also include a transmission radiation source and means for selectively coupling the transmission radiation source to the inner gantry and the first member.

According to another aspect of the present invention, a gamma camera includes a gantry and at least three detectors spaced at substantially equal angular increments about the gantry. The detectors, each of which has a body and a face, define an imaging region adapted to accept the anatomy of a patient. The detectors are arranged for movement between positions which define at least two aperture sizes. At at least one of the aperture sizes, portion of the face of a detector extends beyond the body of another detector.

According to other more limited aspects of the invention, the gamma camera includes means for moving at least one of the detectors in a direction substantially parallel to its face and in a direction substantially orthogonal to its face.

According to another aspect of the invention, the gamma camera comprises a stationary gantry, a rotating gantry, two or more detectors mounted to the rotating gantry for rotation with the gantry, means for rotating the rotating gantry about an axis of rotation, and means for moving at least one of the detectors in a direction tangential to an imaging region.

According to another more limited aspect of the invention, the gamma camera comprises means for moving at least one of the detectors radially with respect to the axis of rotation. The means for moving may comprise a support, a bearing block mounted to the rotating gantry, a bearing rail mounted to the support, and means for sliding the bearing rail in relation to the bearing block.

One benefit of the present invention is that the configuration of the detectors may be readily changed. For example, the detectors may be placed in opposed, orthogonal, and 120 degree configurations. As a result, a single gamma camera may be used in a variety of applications. Another benefit is that the gamma camera may be produced with one or two detectors and readily upgraded to include additional detectors.

The present invention also allows the faces of the detectors to placed near to the patient while allowing relatively large detectors to be used. This improves the image quality of the gamma camera while enhancing the camera's flexibility in multiple applications.

Still yet other benefits and advantages will be appreciated by those skilled in the art upon reading and understanding the following description.

DESCRIPTION

Figure 1:
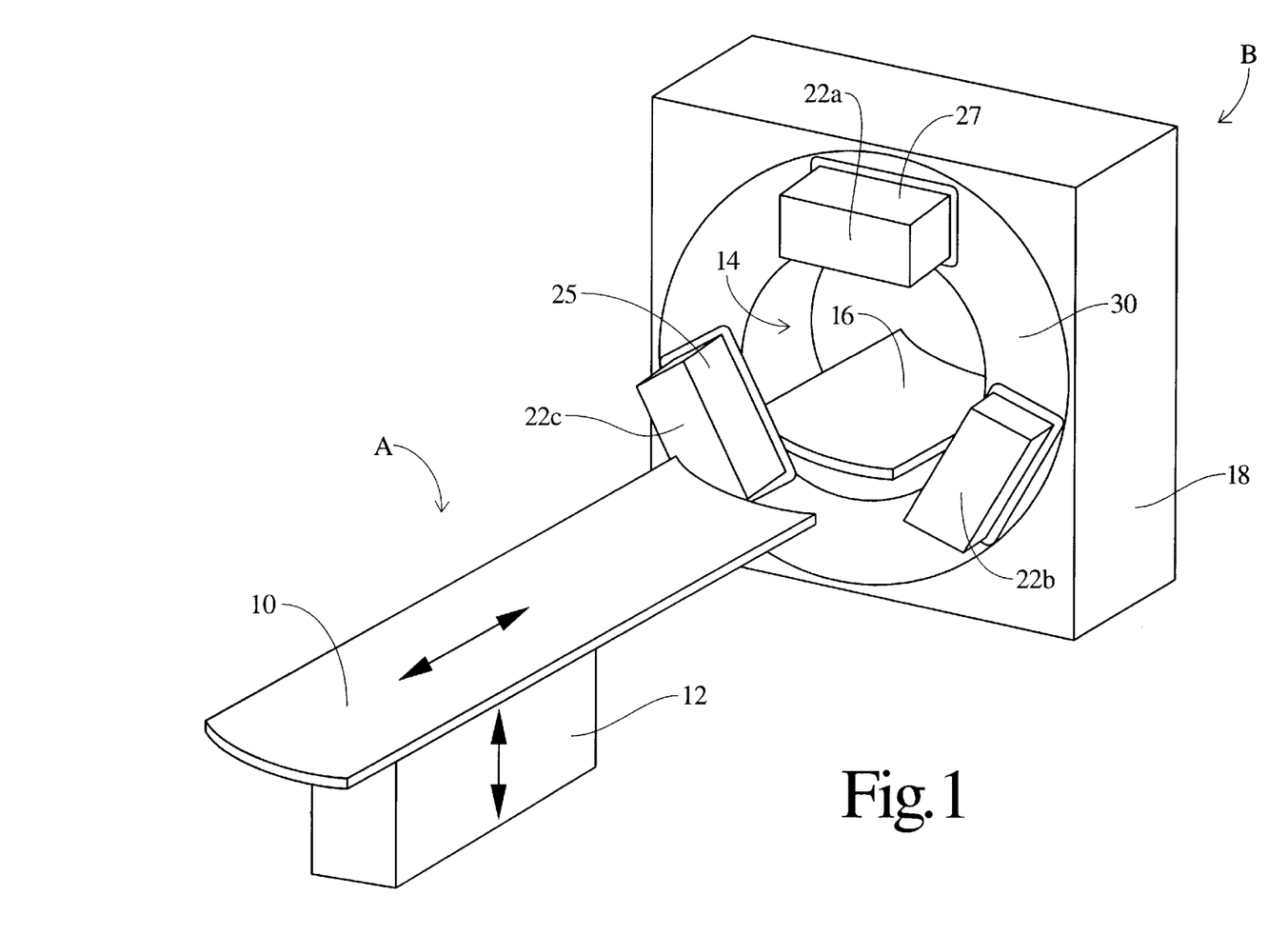
FIG. 1 is a front perspective view of a gamma camera according to the present invention.

With reference to FIG. 1, a patient is supported on a patient support A. The patient support includes a thin, relatively radiation transmissive support surface 10 which is mounted cantilevered from a base 12. The base includes motors for raising and lowering the patient support surface and for extending and retracting the support surface relative to a nuclear camera gantry B.

Figure 2:
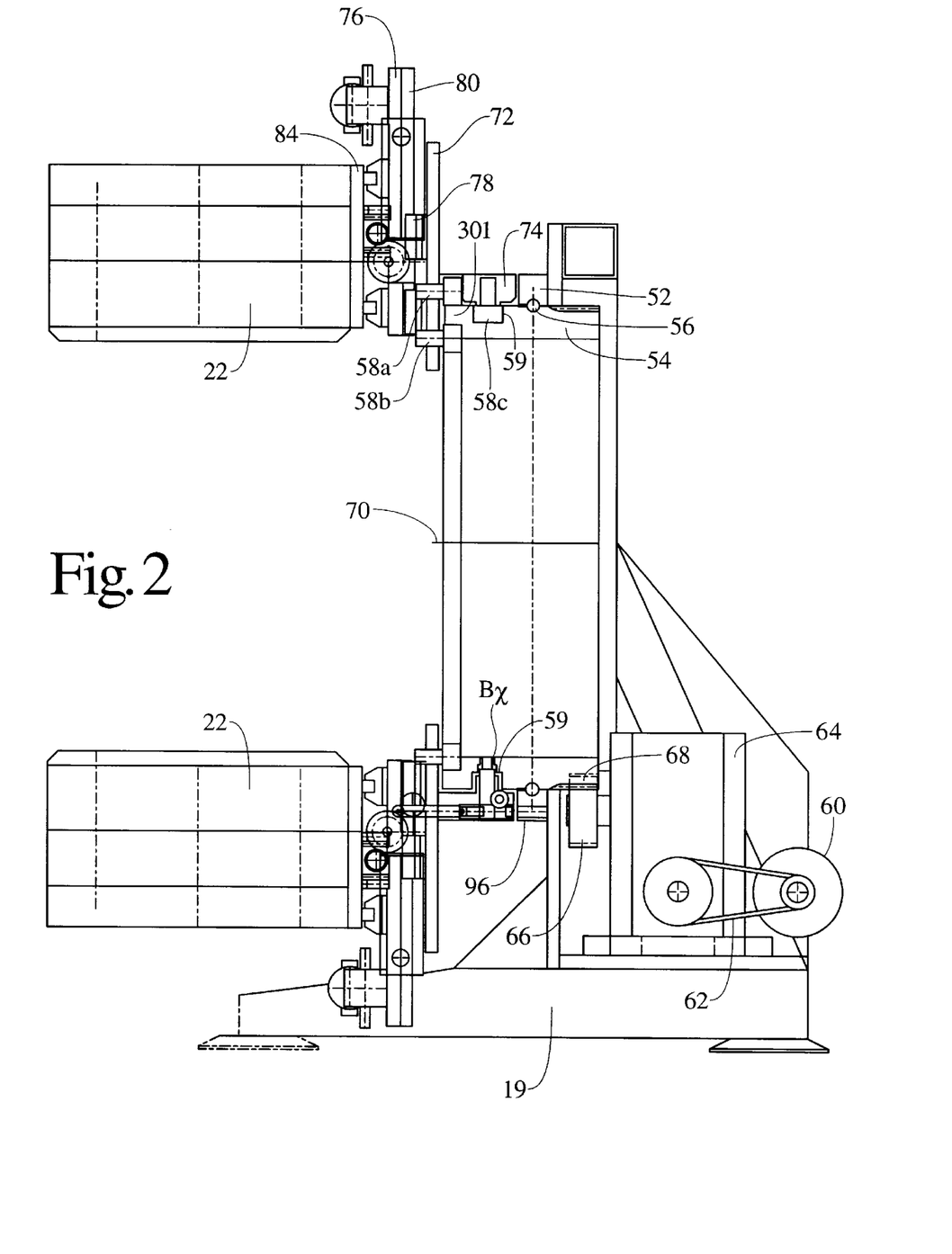
FIG. 2 is a sectional side view of a gamma camera according to the present invention.
Figure 9:
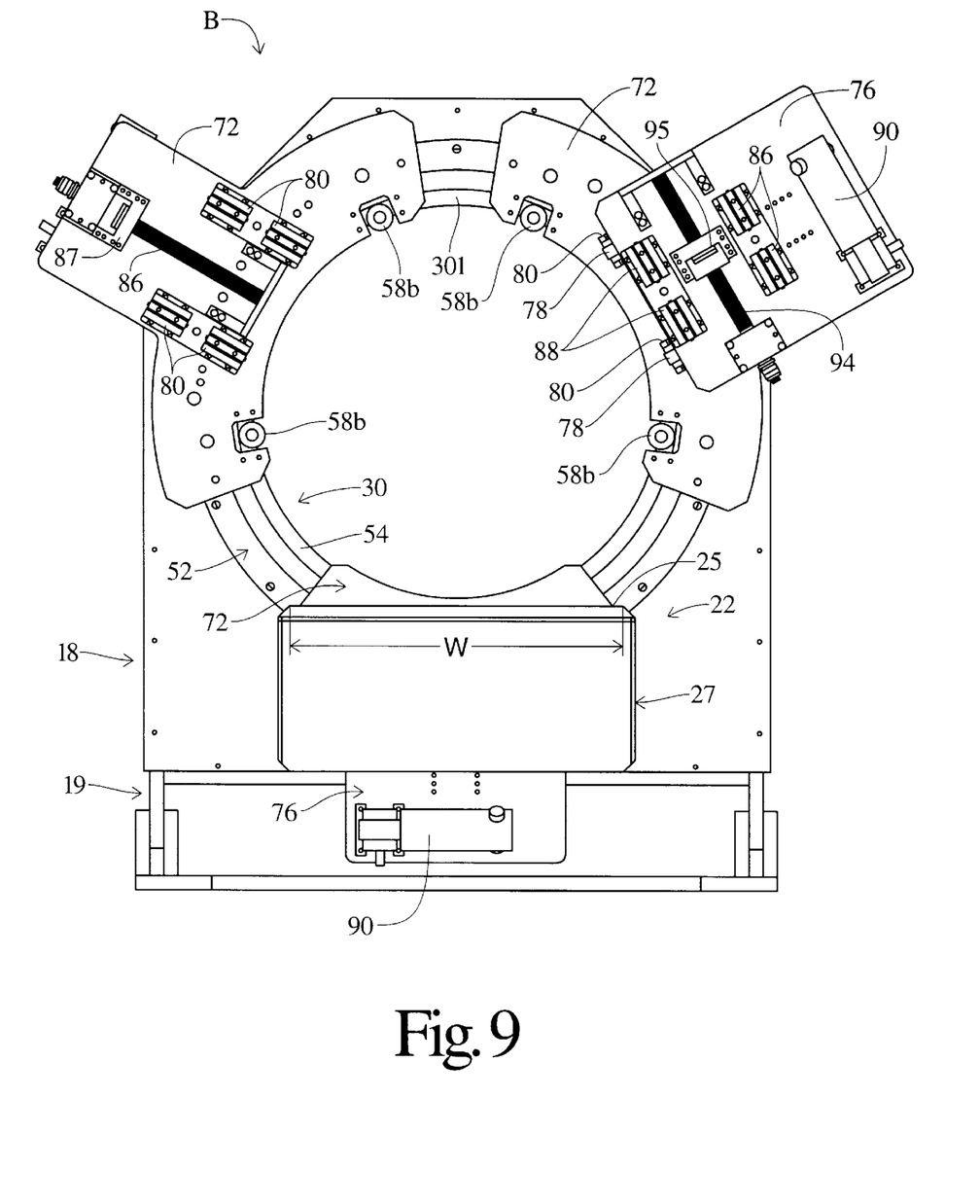
FIG. 9 is a front view of a gantry depicting the various drive mechanisms.

With reference to FIGS. 1, 2, and 9, the gantry B includes stationary 18 and rotating 30 gantry portions which are operatively connected by a bearing having an outer 52 and an inner 54 race. The stationary gantry 18 includes a support frame 19. The outer race 52 of the bearing is fastened to the frame 19.

The rotating gantry structure 30 includes the inner bearing race 54. A raceway 56 between the inner 54 and outer 52 races contains bearings which facilitate rotation of the inner race 54 about an axis of rotation 70. A rotate drive mechanism includes a rotate drive motor 60, belt 62, gearbox 64, and drive pinion 66. The drive pinion 66 engages teeth 68 disposed on the outer circumference of the inner race 54 to rotate the inner bearing race 54 and hence the rotating gantry 30.

Detectors 22a, 22b, 22c are mounted to the rotating gantry portion 30 and define an aperture into which the anatomy of a patient may be inserted. Each detector 22 has a body 27 and a face 25. Each detector is characterized by a width w. As the gantry rotates about the axis of rotation 70, the rotating detectors define a generally circular imaging region, the precise shape of which may vary if the detectors are moved radially during rotation of the gantry 30. As described below, the detectors are mounted to the gantry 30 so as to be movable angularly with respect to the rotating gantry 30, radially toward and away from the axis of rotation 70, and tangentially with respect to the imaging region.

Figure 3:
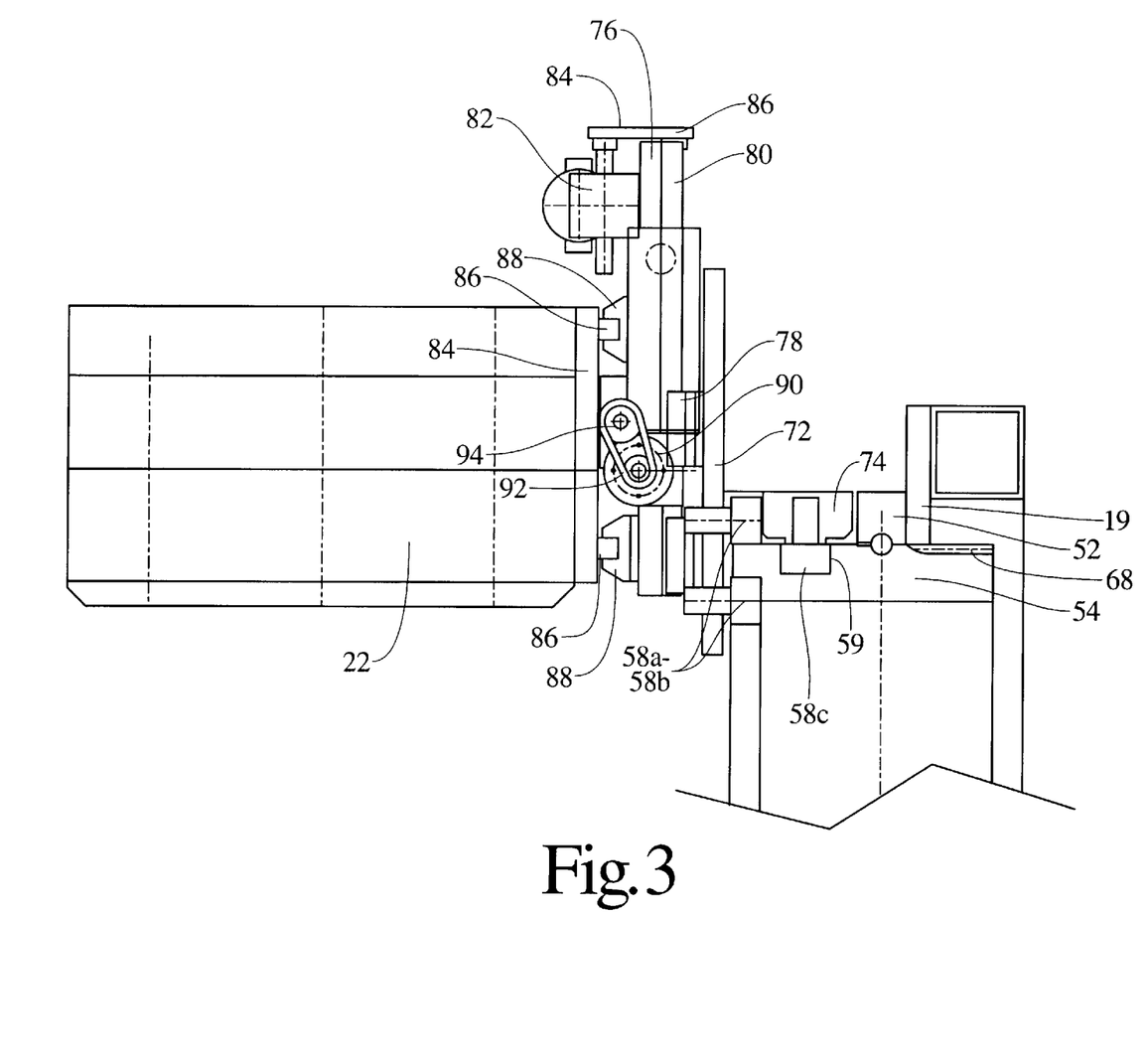
FIG. 3 is an enlarged view of the upper portion of FIG. 2.

Turning now to FIGS. 3 and 9, the inner bearing race 54 supports detector supports 72. The detector supports 72 are rotatably mounted to the inner race 54 using two sets (for a total of four) of shear load cam followers 58a, 58b and four moment load cam followers 58c at spaced angular positions on the support 72. The moment load cam followers 58c are rotatably attached to mounting blocks 74 which are in turn fastened to the detector support 72. The moment load cam followers 58c engage within a groove 59 in the outer circumference of the inner bearing race 54. The shear load cam followers 58a, 58b engage either side of a protrusion 301 on the inner race 54. This arrangement allows the inner bearing race 54 to be rotated with respect to the supports 72 and hence the detectors 22. Viewed from another perspective, the detectors may be moved circumferentially about the inner race 54 to a variety of relative angular positions.

In a gantry having three detectors 22, two of the detectors are movable circumferentially with respect to the race while the third (for example, the detector 22 shown at the bottom or 6 o'clock position in FIG. 9) is attached to the inner race at a fixed angular position. More generally, in a gantry having multiple detectors, one of the detectors is preferably attached to the inner race 52 at a fixed angular position while the remaining detectors are mounted for circumferential motion. As will be appreciated, this arrangement reduces the cost and extra structure associated with the circumferential mounting arrangement.

Radius drives move each of the detectors in direction radially toward and away from the axis of rotation 70. A radius drive support 76 is mounted to each detector support 72. A set of parallel bearing rails 78 is fastened to the radius drive support 76; corresponding bearing blocks 80 are fastened to the detector support 72. A radius drive mechanism, including radius drive gear motor 82, radius drive chain 84, radius drive screw 86, and radius drive block 87 causes the radius drive support 76 to move along the blocks 80 in the radial direction.

Tangential drives move each of the detectors in a direction tangential to the imaging region. A tangential drive support 84 is mounted to each radius drive support 76. A set of bearing rails 86 is fastened to the tangential drive support 84; corresponding bearing blocks 88 are fastened to the radius drive support 76. The tangential bearing blocks 88 and rails 86 are perpendicular to the radius bearing blocks 80 and rails 78. A tangential drive mechanism, including tangential drive gear motor 90, tangential drive chain 92, tangential drive screw 94, and tangential drive block 95 causes the tangential drive support 84 to move along the bearing blocks 88 in a direction tangential to the imaging region.

The detector 22 is fastened to the tangential drive support 84 with its face parallel to the tangential bearing rails 86 and blocks 88 and perpendicular to the radius bearing rails 78 and blocks 80.

Figure 4:
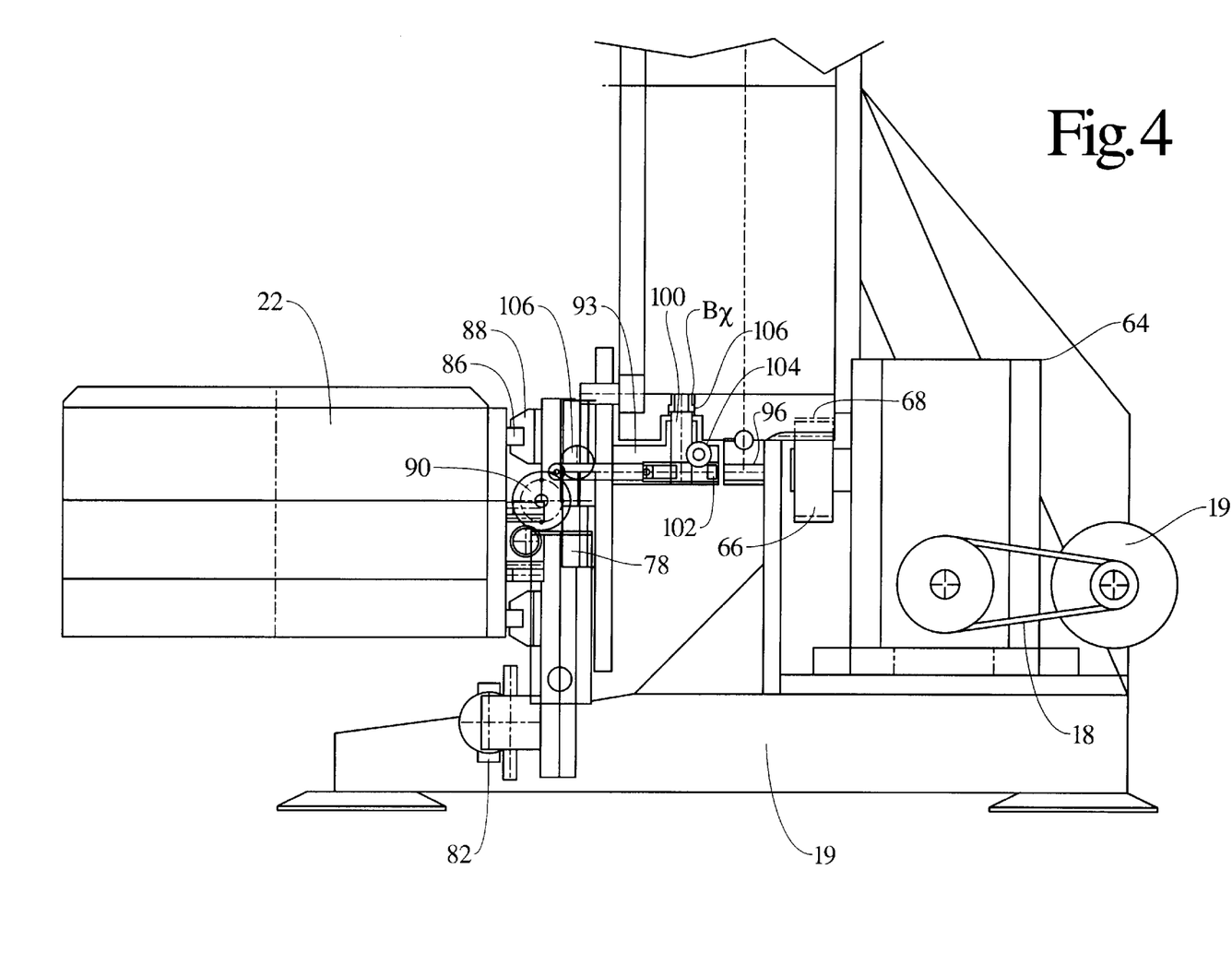
FIG. 4 is an enlarged view of the lower portion of FIG. 2.
Figure 5:
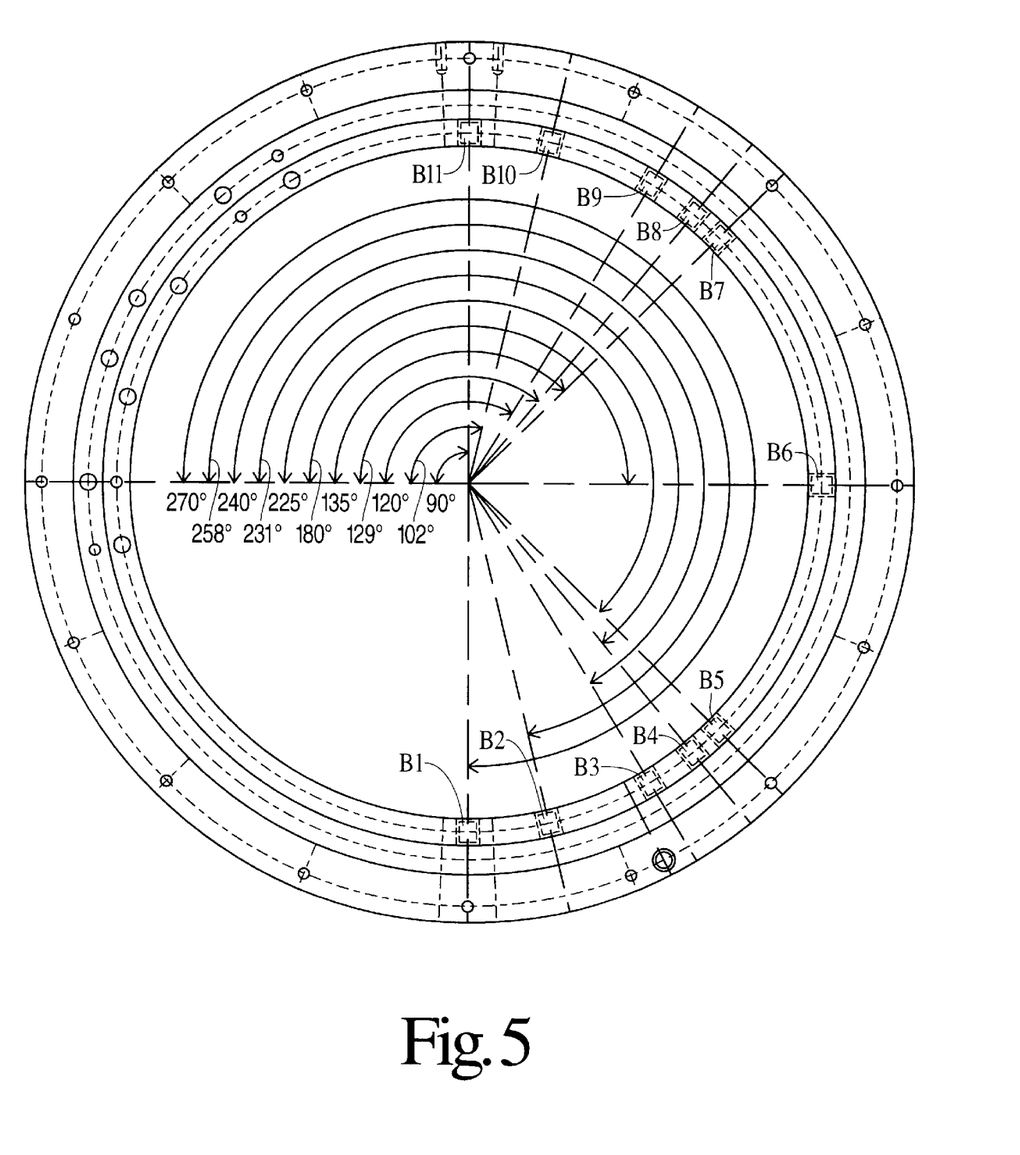
FIG. 5 is a front view of a bearing.
Figure 6:
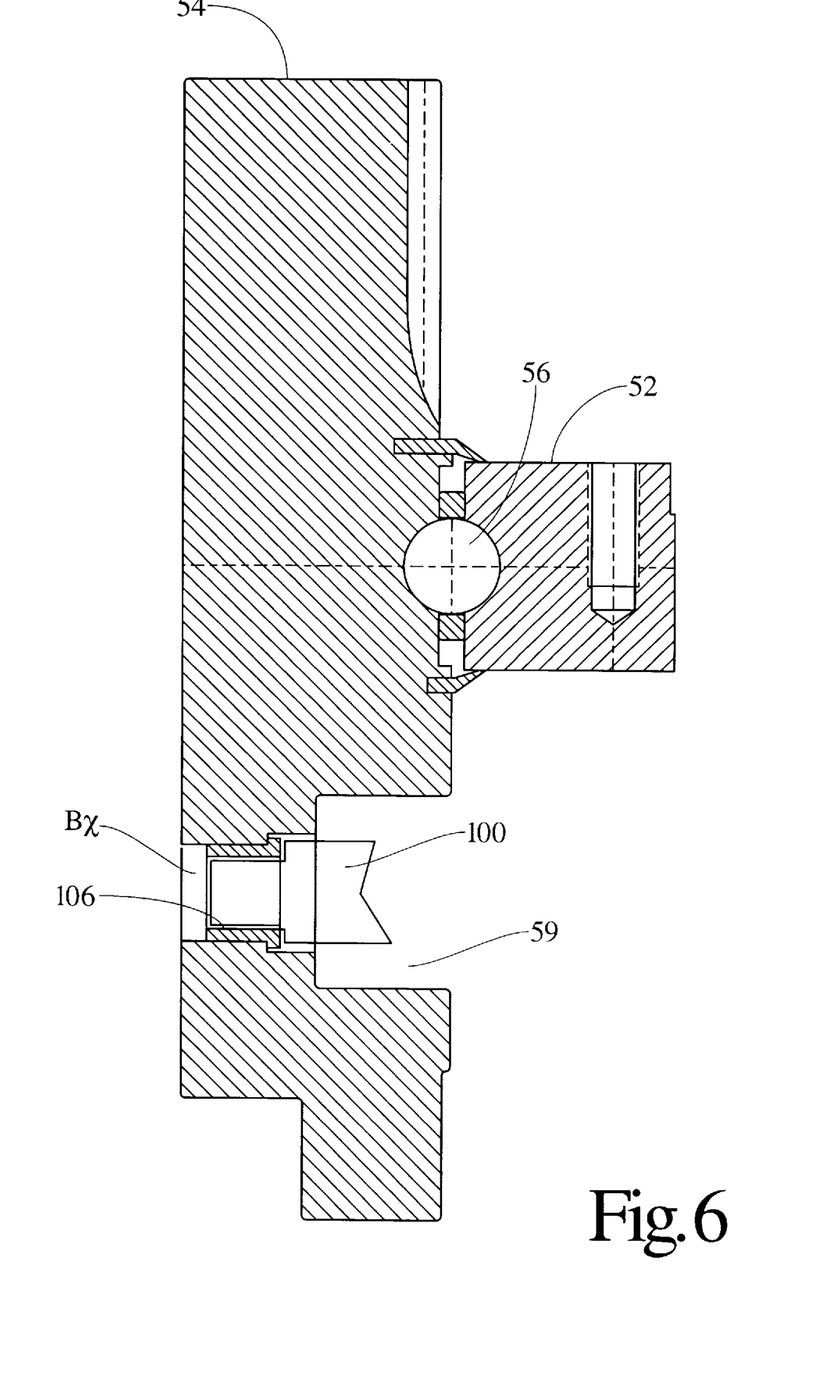
FIG. 6 is a sectional view through 6—6 of FIG. 5.

A coupling mechanism allows the detectors which are movable circumferentially with respect to the inner race 54 to be selectively coupled to the rotating gantry 30 and the stationary gantry 18. With reference to FIGS. 5 and 6, the inner bearing race 54 contains radial bores B1–B11 at various angular positions. The bores $B_x$ are contained in the inner surface of the groove 59 which supports the moment cam follower 58c. With reference to FIGS. 2 and 4, the stationary gantry portion 18 also includes a docking station such as a bore 96 disposed in the outer bearing race 52, preferably at the lowermost or 6 o'clock position.

A locking pin mounting block 98 is fastened to the detector support plate 72 of each circumferentially movable detector. The mounting block in turn supports an inner race locking pin 100 and a frame locking pin 102. The inner race locking pin 100 is movable in a radial direction to engage the radial bores $B_x$. The frame locking pin 102 is movable in a direction to engage the bore 96. The inner race locking pin 100 and the frame locking pin 102 are coupled by a pin to pin drive gear 104. A locking pin actuator 106 mounted to the detector support plate 72 is operatively connected to the frame locking pin 102. FIGS. 2 and 4 show the inner race locking pin 100 engaged in one of the radial bores $B_x$ while frame locking pin 102 is disengaged from the outer race bore 96. In this position, the detector is locked at a fixed angular position on the inner race 52.

The actuator 106 may be energized to urge the frame locking pin 102 to engage the outer race bore 96. Drive gear 104 simultaneously causes the inner race locking pin 100 to retract so that it disengages from the bore $B_x$. In the preferred embodiment, the frame locking pin 102 locks the detector assembly to the outer race 52 before the inner race locking pin 100 disengages from the inner race 54. Similarly, the inner frame locking pin 100 preferably engages the bore $B_x$ before the frame locking pin 102 disengages from the outer race bore 96.

The frame locking pin 102 engages limit switches (not shown) to confirm that the frame locking pin is in the extended or the retracted positions. Proximity switches (not shown) associated with each of the inner race locking bores $B_x$ confirm whether an inner race locking pin is engaged therein. With reference to FIG. 5, each bore includes an insert 106 for accepting the inner race locking pin 100. The locking pin 100 has a stepped, relatively smaller cross section at its distal end. In the event that the distal end of the tip should fail, the section having the larger cos section remains engaged in the bore, thereby continuing to support the detector.

The camera is ordinarily operated with each of the detectors 22 coupled to the inner race 52 for motion with the rotating gantry. To conduct a scan, the rotate drive causes the rotating gantry and each of the detectors 22 to rotate together as a unit about the imaging region.

The configuration of the detectors may be adjusted by rotating the inner race 52 until a desired circumferentially movable detector 22 reaches the 6 o'clock position. Locking pin actuator 106 extends the frame locking pin 100 into the outer race bore 96 and retracts the inner race locking pin 100 from the bore $B_x$ to couple the detector to the docking station and free it from the rotating gantry 30. The inner race 52 is rotated to a desired position, i.e., until the inner race locking pin 100 is aligned with the desired inner race bore $B_x$. The inner race locking pin 100 is extended into the bore $B_x$; the frame locking pin 102 is retracted from the outer race bore 96 such that the detector 22 is coupled to the inner race 54 in its new angular position. This process is repeated until each of the movable detectors is placed in a desired angular position.

Examples of detector configurations are shown in FIGS. 7a–7i. Table 1 depicts the bore $B_x$ associated with each detector head for the configurations of FIG. 7. The detector configurations shown in FIG. 7 and Table 1 are not exhaustive.

TABLE 1

| FIG. | Detector 2 | Detector 3 |
|------|------------|------------|
| 7a   | B9         | B3         |
| 7b   | B11        | B1         |
| 7c   | B11        | B5         |
| 7d   | B10        | B4         |
| 7e   | B7         | B1         |
| 7f   | B8         | B2         |
| 7g   | B11        | B5         |
| 7h   | B10        | B4         |
| 7i   | B6         | x          |

Figure 7:
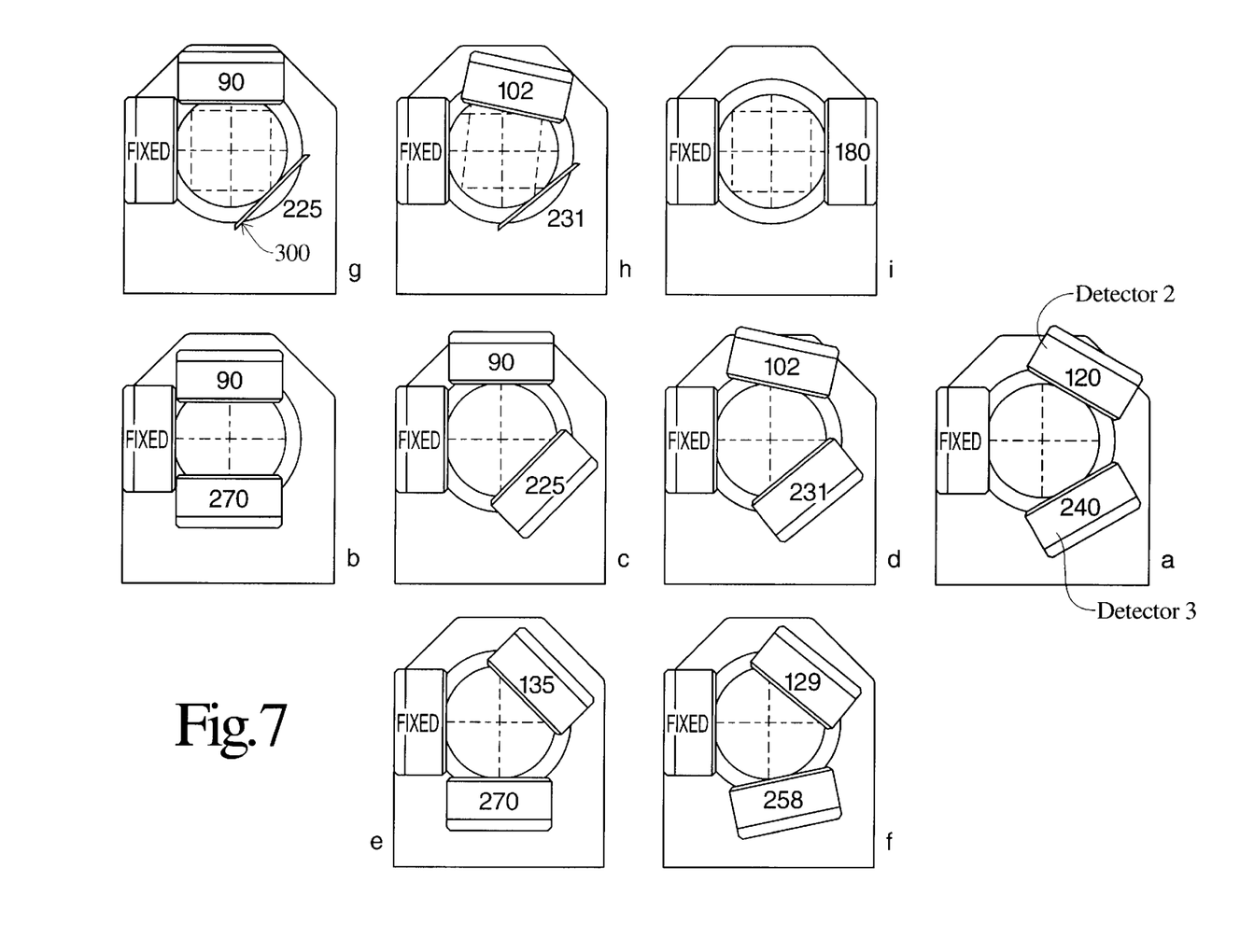
FIGS. 7a–7i are front views of a gantry depicting various detector configurations.

FIGS. 7a–7f depict configurations for a three detector gantry. FIG. 7b shows a three detector gantry with two of the detectors configured in a 180 degree opposed configuration. The opposed detectors provide anterior and posterior images. The third detector produces a lateral image which provides depth information. As shown in FIGS. 7g and 7f, a transmission radiation source 300 may be substituted for one of the detectors. FIG. 7i depicts a system having two heads configured in a 180 degree opposed configuration. Of course, four or more detectors can also be accommodated. Note that FIG. 7 and Table 1 are not an exhaustive list of the possible configurations. Other desirable configurations may readily be implemented by placing bores $B_x$ in other angular positions of by using different combinations of bores $B_x$.

Similarly, the two detectors in a two detector gantry can be placed at any of the angular positions shown in FIG. 7. Thus, a two detector gantry can be configured, for example, in 180 degree opposed, 90 degree orthogonal, or 102 degree orthogonal positions.

Figure 8:
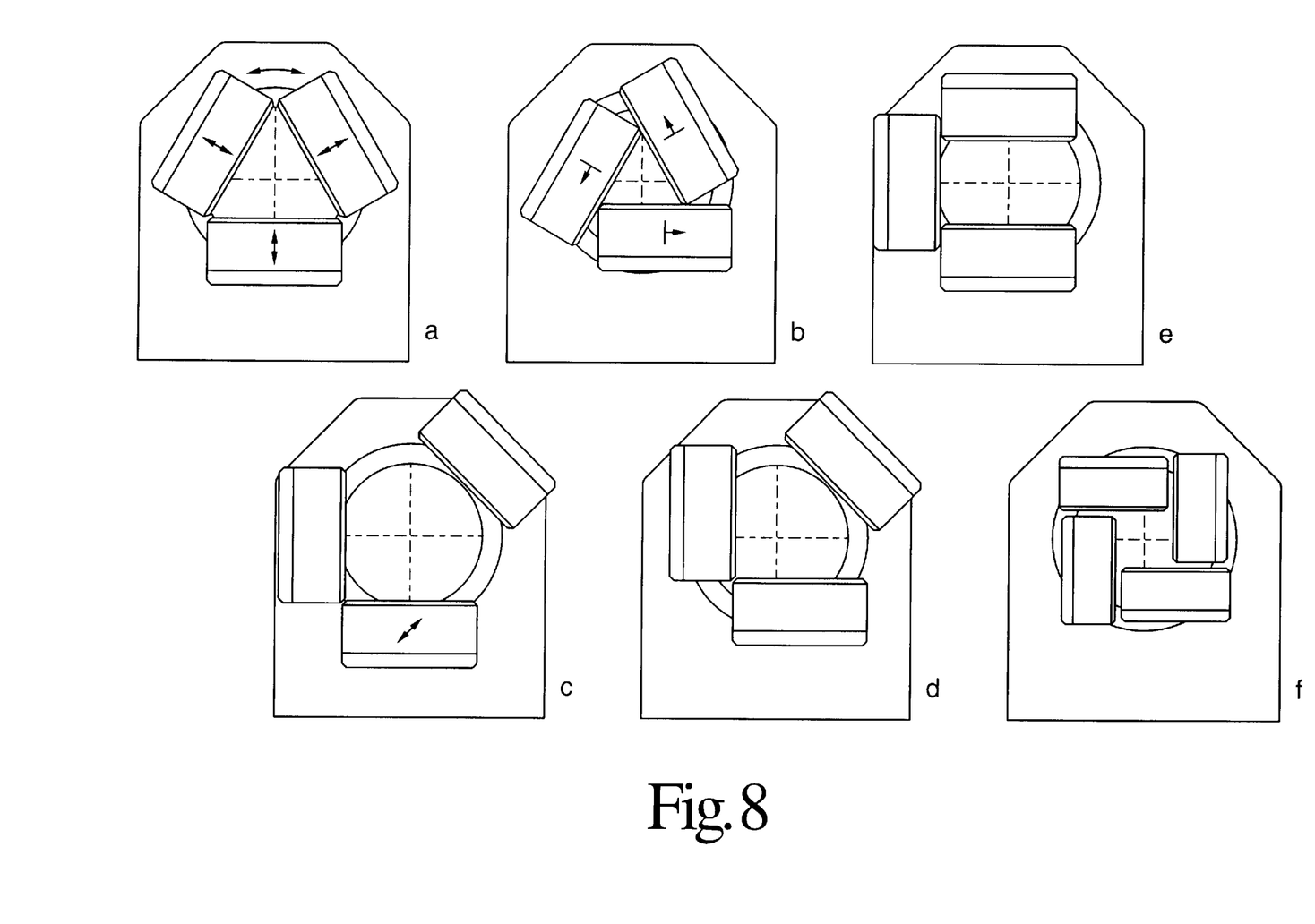
FIGS. 8a–8f are front views of a gantry depicting various detector configurations.

As depicted by the radial arrows in FIG. 8a, the radial drives move the detectors 20 radially toward and away from the imaging region. As can be seen, the minimum aperture size and hence the minimum distance between the faces of the detectors and the patient is limited by the width of the detectors. The present invention permits the detectors 22 to be irised so that the minimum distance between the detector faces and the patient can be reduced from the limit otherwise defined by the detector widths. As depicted by the tangential arrows in FIG. 8b, the tangential drives permit the detectors to be moved in a direction generally tangential to the imaging region. As a result, mechanical interference between the corners of the detectors can be avoided, and the radial drives can be used to place the faces of the detectors closer to the patient. As shown in FIG. 8b, a portion of each detector face extends beyond the body of another detector. As will be appreciated, the width of each side of the aperture has a dimension smaller than the width of the corresponding detector. In this way, the detectors may be positions to define a variety of different aperture sizes. A four detector gantry is depicted in FIG. 8f.

FIGS. 8c and 8d depict a three detector gantry having two detectors arranged in a 90 degree configuration which is especially efficient for cardiac imaging. As shown in FIG. 8c, the minimum distance between the detector heads is ordinarily limited by the size of the detectors 20. Using a combination of tangential and radial motion which produces motion in the direction depicted by the arrows in FIG. 8c, however, the detectors can be positioned much nearer to the axis of rotation as shown in FIG. 8d.

The invention has been described with reference to the preferred embodiment. Obviously, modifications and alterations will occur to others upon reading and understanding the preceding description. It is intended that the invention be construed as including all such modifications and alterations insofar as they come within the scope of the appended claims or the equivalents thereof Having disclosed the preferred embodiment, the invention is now claimed to be:

1. A gamma camera comprising:
    a first member;
    a rotating gantry;
    two or more detectors;
    means for rotating the rotating gantry with respect to the first member; and
    means for selectively coupling at least one of the detectors to the to the first member and the rotating gantry such that the rotating gantry may be rotated with respect to the detector when the detector is coupled to the first member and the detector rotates with the rotating gantry when coupled to the rotating gantry.

2. The gamma camera of claim 1 wherein the means for selectively coupling comprises a locking pin.

3. The gamma camera of claim 2 wherein the rotating gantry comprises one or more bores adapted to receive the locking pin.

4. The gamma camera of claim 3 wherein the locking pin comprises portions having a larger and a smaller cross section the smaller cross section being disposed at the distal end of the locking pin.

5. The gamma camera of claim 1 comprising:
    three detectors, the first detector being mounted in a fixed angular position with respect to the rotating gantry; and
    means for selectively coupling the second and third detectors to the first member and the rotating gantry such that the rotating gantry may be rotated with respect to the second and third detectors when the second and third detectors are coupled to the first member and the second and third detectors rotate with the rotating gantry when coupled to the rotating gantry.

6. The gamma camera of claim 1 wherein each detector is movable in a direction substantially parallel to its face.

7. The gamma camera of claim 1 wherein each detector is movable in a direction substantially perpendicular to its face.

8. The gamma camera of claim 1 further comprising:
    a transmission radiation source;
    means for selectively coupling the transmission radiation source to the rotating gantry and the first member such that the rotating gantry may be rotated with respect to the transmission radiation source when the transmission radiation source is coupled to the first member and the transmission radiation source rotates with the rotating gantry when coupled to the rotating gantry.

9. The gamma camera of claim 1 wherein the first member is a stationary gantry.

10. A gamma camera comprising:
    a rotating gantry selectively rotatable about an imaging region;
    a first detector;
    means for rotating the rotating gantry about the imaging region; and
    means for selectively coupling the first detector to and selectively decoupling the first detector from the rotating gantry such that the first detector rotates about the imaging region in response to rotation of the rotating gantry when coupled to the rotating gantry but does not rotate about the imaging region in response to rotation of the rotating gantry when decoupled from the rotating gantry.

11. The gamma camera of claim 10 wherein the gamma camera comprises a first member and further comprising means for selectively coupling the first detector to the first member.

12. The gamma camera of claim 11 wherein the first member is a stationary gantry.

13. The gamma camera of claim 10 wherein the first detector remains at a fixed angular position with respect to the rotating gantry when coupled thereto, the gamma camera further comprising:
    a second detector mounted in a fixed angular position with respect to the rotating gantry for rotation therewith;
    a docking station;
    means for selectively coupling the first detector to the docking station;
    means for rotating the rotating gantry about the axis of rotation whereby, when the first detector is coupled to the docking station, the rotating gantry may be rotated until the first and second detectors reach a desired relative angular position and whereby, when the first and second detectors have reached the desired relative angular position, the first detector may be coupled to the rotating gantry for rotation therewith.

14. The gamma camera of claim 10 wherein the gamma camera has an imaging region and further comprising means for moving the first detector in a direction tangential to the imaging region and radially with respect to the axis of rotation.

15. A method for transforming the configuration of a gamma camera having a rotating gantry selectively rotatable about an axis of rotation and a first detector selectively coupleable to the rotating gantry for rotation therewith, the method comprising the steps of:
    uncoupling the first detector from the rotating gantry;
    rotating the rotating gantry about the axis of rotation; and
    coupling the first detector to the rotating gantry.

16. The method of claim 15 wherein the gamma camera comprises a docking station, the method further comprising the step of coupling the first detector to the docking station.

17. The method of claim 15 wherein the rotating gantry comprises a bore and the step of uncoupling the first detector comprises the step of retracting a locking pin from the bore.

18. The method of claim 15 wherein the gamma camera comprises a second detector coupled to the rotating gantry and wherein the step of rotating comprises rotating the rotating gantry until the first and second detectors reach a desired relative angular position with respect to the rotating gantry.

19. The method of claim 18 further comprising the steps of:

uncoupling the second detector from the rotating gantry;

rotating the rotating gantry about the axis of rotation until the first and second detectors reach a desired relative angular position; and coupling the second detector to the rotating gantry.

20. The method of claim 18 wherein the desired relative angular position is 120 degrees.

21. A gamma camera comprising:

a stationary frame;

a rotating gantry;

a first detector coupled to the rotating gantry;

a second detector;

means for selectively coupling the second detector to the rotating gantry and the stationary frame to vary the relative angular position of the detectors about the rotating gantry.

22. A method of varying the configuration of a gamma camera including a rotating member selectively rotatable about an imaging region, first and second detectors, and a stationary member, the first and second detectors being coupled to the rotating member for rotation therewith, the method comprising the steps of:

uncoupling the second detector from the rotating member;

coupling the second detector to the stationary member;

rotating the rotating member until the first and second detectors reach a desired relative angular position;

uncoupling the second detector from the stationary member;

coupling the second detector to the rotating member for rotation therewith.

23. The method of claim 22 wherein the relative angular position is 90 degrees.

24. The method of claim 22 wherein the relative angular position is 102 degrees.

25. The method of claim 22 wherein the relative angular position is 120 degrees.

26. The method of claim 22 wherein the relative angular position is 180 degrees.

27. The method of claim 22 wherein the relative angular position is 135 degrees.

28. The method of claim 22 further comprising the step of rotating the rotating member until the second detector is located at a 6 o'clock position prior to uncoupling the second detector from the rotating member.

29. The method of claim 22 wherein the gamma camera comprises a third detector, the method further comprising the steps of:

uncoupling the third detector from the rotating member;

coupling the third detector to the stationary member;

rotating the rotating gantry until the second and third detectors reach a desired relative angular position;

uncoupling the third detector from the stationary member;

coupling the third detector to the rotating member for rotation therewith.

30. The method of claim 29 wherein the desired angular position between the second and third detectors is 120 degrees.

31. The method of claim 22 wherein the step of coupling the second detector to the rotating member comprises the step of inserting a locking pin in an aperture located on the rotating member.

32. The method of claim 22 wherein the gamma camera comprises a transmission radiation source, the method further comprising the steps of:

uncoupling the transmission radiation source from the rotating member;

coupling the transmission radiation source to the stationary member;

rotating the rotating gantry until the transmission radiation source reaches a desired relative position with respect to at least one of the first and second detectors; and coupling the transmission radiation source to the rotating member for rotation therewith.

33. A gamma camera comprising:

a rotating gantry portion, the rotating gantry portion being selectively rotatable about an imaging region and adapted to receive a coupling device at at least first and second angular positions;

a first detector assembly coupled to the rotating gantry portion at a third angular position such that rotation of the rotating gantry portion causes the first detector to rotate about the imaging region; and a second detector assembly;

a coupling device operatively connected to the rotating gantry portion and the second detector assembly and having a coupled position wherein rotation of the rotating gantry portion causes the second detector assembly to rotate about the imaging region and a decoupled position wherein rotation of the rotating gantry does not cause the second detector assembly to rotate about the imaging region;

an actuator operatively connected to the coupling device so as to selectively urge the coupling device between the coupled and decoupled positions;

whereby the relative angular positions of the first and second detector assemblies may be selectively varied.

34. The apparatus of claim 33 wherein the coupling device comprises a first pin and the rotating gantry portion comprises a plurality of apertures adapted to receive the first pin when the coupling device is in the coupled position.

35. The apparatus of claim 34 wherein the coupling device comprises a second pin and the and the gamma camera comprises a stationary gantry portion having a docking aperture adapted to receive the second pin when the coupling device is in the uncoupled position.

36. The apparatus of claim 33 wherein the actuator is mounted to the second detector assembly.

* * * * *